(12) United States Patent
Jeffrey et al.

(10) Patent No.: US 6,777,226 B2
(45) Date of Patent: Aug. 17, 2004

(54) SENSOR DEVICE FOR DETECTING MICROORGANISMS, AND METHOD THEREFOR

(75) Inventors: Scott R. Jeffrey, Raleigh, NC (US);
Paul M. Matsumura, Cary, NC (US);
Martin J. Maresch, Durham, NC (US);
Jones M. Hyman, Durham, NC (US);
Thurman C. Thorpe, Durham, NC (US)

(73) Assignee: bioMerieux, Inc., Durham, NC (US)

( * ) Notice: Subject to any disclaimer, the term of this patent is extended or adjusted under 35 U.S.C. 154(b) by 534 days.

(21) Appl. No.: 09/741,402

(22) Filed: Dec. 18, 2000

(65) Prior Publication Data

US 2003/0100104 A1 May 29, 2003

Related U.S. Application Data (63) Continuation of application No. 09/320,386, filed on May 27, 1999, now Pat. No. 6,197,577, which is a continuation of application No. 08/989,560, filed on Dec. 12, 1997, now Pat. No. 5,976,827.

(51) Int. Cl.⁷ .............................................. C12M 1/34
(52) U.S. Cl. ............................ 435/287.7; 435/287.8; 435/287.9; 435/288.3; 435/288.7
(58) Field of Search ............................ 435/30, 31, 32, 435/34, 287.1, 287.4, 287.7, 287.8, 287.9, 288.1, 288.3, 288.7

(56) References Cited

U.S. PATENT DOCUMENTS

| | | |
|---|---|---|
| 3,856,628 A | 12/1974 | Sbarra |
| 3,962,040 A | 6/1976 | Campbell et al. |
| 4,280,002 A | 7/1981 | Bailey et al. ............... 435/298 |
| 4,468,456 A | 8/1984 | Deyloff ........................ 435/36 |
| 4,565,783 A | 1/1986 | Hansen et al. .............. 435/299 |

(List continued on next page.)

FOREIGN PATENT DOCUMENTS

| | | |
|---|---|---|
| JP | 62272967 | 5/1986 |
| SU | 1359301 | 12/1987 |
| WO | WO99/29831 | 6/1999 |

OTHER PUBLICATIONS

US 4,476,226, 10/1984, Hansen et al. (withdrawn)

LiMuti et al., *Journal of Microbiological Methods*, 9:129–137, 1989.

(List continued on next page.)

*Primary Examiner*—David A. Redding
(74) *Attorney, Agent, or Firm*—Myers Bigel Sibley & Sajovec (57) ABSTRACT

A device and method allow for detecting the presence of microorganisms in clinical and non-clinical specimens. The device, a sensor, provides an environment to culture microbial organism colonies from a fluid sample, and a means to facilitate microbial detection and quantification, either manually or with an instrument. The sensor has a microorganism immobilization matrix layer and a sensor layer. Detected microbial colonies are immediately available for further testing. The sensor provides an area for accepting a fluid sample, a mechanism to immobilize the fluid sample on an interior surface of the plate, nutrients to facilitate growth of microorganisms in the sample, and a sensor for allowing the detection and/or enumeration of microorganism colonies within the sample.

22 Claims, 5 Drawing Sheets

U.S. PATENT DOCUMENTS

| | | | |
|---|---|---|---|
| 5,089,413 A | 2/1992 | Nelson et al. | 435/284 |
| 5,094,955 A | 3/1992 | Calandra et al. | 435/291 |
| 5,137,812 A | 8/1992 | Matner | 435/38 |
| 5,232,838 A | 8/1993 | Nelson et al. | 435/30 |
| 5,364,766 A | 11/1994 | Mach et al. | 435/34 |
| 5,403,722 A | 4/1995 | Floeder et al. | 435/39 |
| 5,409,838 A | 4/1995 | Wickert | 436/8 |
| 5,443,963 A | 8/1995 | Lund | 435/34 |
| 5,462,860 A | 10/1995 | Mach | 435/34 |
| 5,464,755 A | 11/1995 | Bochner | 433/34 |
| 5,510,246 A | 4/1996 | Morgan | 435/39 |
| RE35,286 E | 6/1996 | Nelson et al. | 435/243 |
| 5,541,082 A | 7/1996 | Botchner | 435/34 |
| 5,573,950 A | 11/1996 | Graessle et al. | 435/287.3 |
| 5,627,045 A | 5/1997 | Bochner et al. | 435/34 |
| 5,681,712 A | 10/1997 | Nelson | 435/30 |
| 5,912,115 A | 6/1999 | Hyman et al. | 435/4 |
| 5,976,827 A * | 11/1999 | Jeffrey et al. | 435/34 |
| 6,197,577 B1 * | 3/2001 | Jeffrey et al. | 435/288.7 |

OTHER PUBLICATIONS

Y. Umemoto, *Agr. Biol. Chem.*, 33:11:1651–1653, 1969.

Y. Yamazaki et al., *Z. Naturforsch*, 42c:1082–1088, 1987.

Y. Umemoto et al., *Milchwissenschaft*, 30(10):591–594, 1975.

N. Belayev et al., *J. of Biochem. and Biophys. methods*, 25:125–132, 1992.

P. Jones et al., *Nucleic Acids Research*, 20:17:4599–4606, 1992.

A. Gavoille et al., *COmput. Boil. Med.*, 24:3:179–188, 1994.

A. Singh et al., *Applied and Enviromnmental Microbiology*, 56:2:389–394, 1990.

S. Hammonds et al., *Letters in Applied Microbiology*, 10:27–29, 1990.

S. Eins, *Microscope*, 22:59–68, 1974.

M. Calicchia et al., *Journal of Food Protection*, 57:10:859–864, 1994.

M. Fernandes et al., *CABIOS*, 4:2:291–295, 1988.

J. Leyden et al., *Journal of Hospital Infection*, 18B:13–22, 1991.

R. Mueller et al;., *Biotechnology and Bioengineering*, 39:11:1161–1170, 1992.

M. Smith et al, *In Vitro Cellular and Decelopmental Biology*, 23:1:67–74, 1987.

"3M Pertifilm Test Kit–HEV" Product Information Sheet.

"Petrifilm™ Test Kit—HEC" Product Insert.

3M, "Lift your lab to a new level of efficiency", Product Sheet.

3M "Petrifilm™ Enterobacteriaceae Count Plates" Product Sheet, 1991.

* cited by examiner

SENSOR DEVICE FOR DETECTING MICROORGANISMS, AND METHOD THEREFOR

RELATED APPLICATIONS

This application is a continuation of U.S. application Ser. No. 09/320,386, filed May 27, 1999, now U.S. Pat. No. 6,197,577 which is a continuation of U.S. application Ser. No. 08/989,560, filed Dec. 12, 1997, now U.S. Pat. No. 5,976,827. The contents of these applications are hereby incorporated by reference as if recited in full herein.

BACKGROUND OF THE INVENTION

The presence of microbial contamination in clinical specimens is conventionally determined by culturing the specimens in the presence of nutrients and detecting microbial activity through changes in the specimen or in the atmosphere over the specimen after a period of time. For example, in U.S. Pat. No. 4,182,656 to Ahnell et al., the sample is placed in a container with a culture medium comprising a carbon 13 labeled fermentable substrate. After sealing the container and subjecting the specimen to conditions conducive to biological activity, the ratio of carbon 13 to carbon 12 in the gaseous atmosphere over the specimen is determined and compared with the initial ratio. In U.S. Pat. No. 4,152,213, a method is claimed by which the presence of oxygen consuming bacteria in a specimen is determined in a sealed container by detecting a reduction in the amount of oxygen in the atmosphere over the specimen through monitoring the pressure of gas in the container. U.S. Pat. No. 4,073,691 provides a method for determining the presence of biologically active agents, including bacteria, in a sealed container containing a culture medium by measuring changes in the character if the gaseous atmosphere over the specimen after a period of time.

A method for non-invasive detection is taught by Calandra et al., U.S. Pat. No. 5,094,955, where a device is disclosed for detecting the presence of microorganisms in clinical specimens, such as blood or other body fluids, and in non-clinical specimens, by culturing the specimens with a sterile liquid growth medium in a transparent sealed container. The presence of microorganisms is determined by detecting or measuring changes in the pH of the specimen or the production of carbon dioxide within the specimen using a sensor affixed to the interior surface of the container or to the sealing means used to seal the container. In Calandra et al., microorganisms can be detected in the presence of interfering material, such as large concentrations of red blood cells, through non-radiometric and non-invasive means.

One disadvantage of the detection system of Calandra et al. is that the time required for detecting the presence of microorganisms is related to the number or microorganisms within the sample. Also, because the growth medium for the microorganisms is a liquid, the container must usually be agitated during incubation, which is an additional expense involved in making the incubation equipment, as well as an increase in the likelihood of a mechanical breakdown. Also, such a system allows for the determination of the presence of microorganisms, but does not allow for enumeration. Furthermore, it is often the case that after detection of microorganisms, it is desired to identify the microorganisms and/or determine their susceptibility to various antibiotics. In a Calandra-type system, it would be necessary to plate out the microorganisms from the liquid culture medium before performing susceptibility or identification tests, which involves additional time—time that is not always available if the patient is very ill.

SUMMARY OF THE INVENTION

The present invention relates to a device and method for detecting the presence of microorganisms in clinical and non-clinical specimens. The device, hereinafter referred to as the "sensor plate", provides an environment to culture microbial organism colonies from a liquid sample, and a means to facilitate microbial detection and quantification, either manually or with an instrument. The sensor plate comprises a solid, semi-solid or powdered gel immobilization matrix layer and a sensor layer. Detected microbial colonies are isolated and immediately available for further testing.

More particularly, the sensor plate provides an area for accepting an unknown liquid sample (unknown whether microorganisms are present or not) a mechanism to immobilize the liquid sample on an interior surface of the plate, components (e.g. nutrients) to facilitate growth of microorganisms in the sample, and a sensor for allowing the detection and enumeration of microorganism colonies within the sample. The sensor plate can be comprised of an immobilization layer (e.g. a gel layer) and a sensor layer, with a sample being absorbed into, or forming a gel with, the immobilization matrix layer. A sensor layer can be located on at least one surface of the sensor plate to indicate the presence of microorganisms. Small areas or zones of color changes occur in the sensor layer which indicate actual microorganism colony growth in the immobilization layer. The sensor plate is inspected manually or automatically with an instrument to determine the presence, location and/or number of microorganism colonies.

Various other features and advantages of the invention will become apparent from the detailed description below taken in conjunction with the accompanying drawings and the appended claims.

DETAILED DESCRIPTION OF THE PREFERRED EMBODIMENTS

Figure 1:
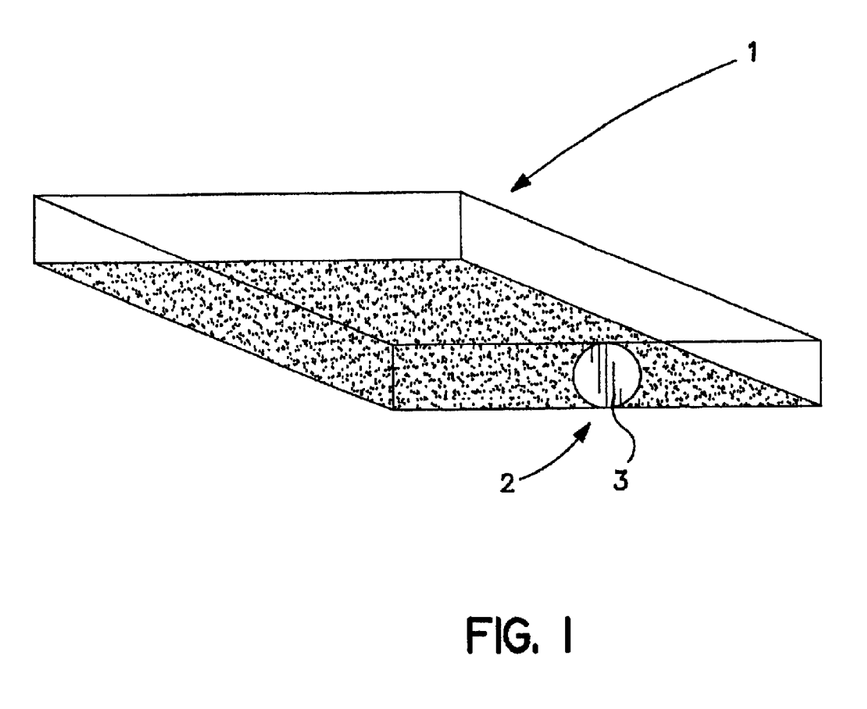
FIG. 1 is an illustration of the sensor plate device.

FIG. 1 is an illustration of sensor plate 1 which can be in the form of a flat, shallow container with at least one side (e.g. the bottom side) being transparent or translucent. Though the container can be open (or even simply a substrate), it is preferably a sealed or sealable container, and preferably with an amount of headspace above the sensor plate layers. The container can be provided with a port 2, which may be sealed with a stopper 3, screw-cap, septum, or any combination thereof (or any other sealing device). Once a sample is collected into the container, the sensor plate can be configured as either a gas-permeable or a gas-impermeable container, depending on the growth requirements of the microorganism. This configuration is accomplished by using different plate composition materials, laminates (gas impermeable and/or hydrophobic gas-permeable membranes), and/or configurable vents (e.g. a gas permeable membrane in an opening of the container wall).

Figure 2:
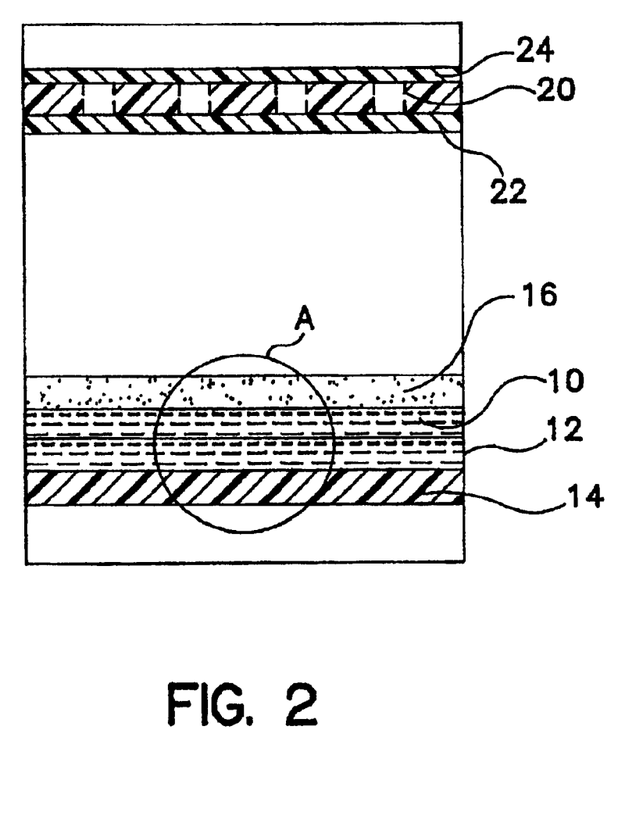
FIG. 2 is a cross section of the sensor plate device.

Within the container of the sensor plate device, are one or more layers which help to immobilize/absorb the sample so that colonies of microorganisms can grow localized which increases the ability to detect the colonies of microorganisms. In one embodiment, at least one layer in the device has matrixes which adversely affect visualization of microorganisms. As can be seen in FIG. 2, provided are an immobilizing layer (matrix layer) 10 and a sensor layer 12. These two layers, which will be described more fully hereinafter, can also be combined together into a single layer, though it is preferred that the two layers be provided separately. As also shown in FIG. 2, is the plate bottom 14, which is preferably transparent for viewing/imaging changes in the sensor layer due to microorganism growth.

The sensor layer 12 is provided for the purpose of indicating the location of microbial growth by providing a tightly localized dramatic change in the ultraviolet, visible, and/or infrared spectrum. This localized change is detectable on the bottom surface of the plate, opposite the sensor surface near the microbial growth. The sensor layer comprises a material that undergoes a change in a detectable property (e.g. an indicator) which is embedded on and/or in a matrix (support material) which is preferably opaque. By "opaque", it is meant that the sensor layer sufficiently blocks the viewing or detecting (in any relevant electromagnetic region) of the test sample and/or actual microorganism colonies immobilized in the immobilization layer from the opposite side of the sensor layer (e.g. semi-opaque, substantially opaque, or fully opaque). Though it is possible to have a transparent or relatively transparent sensor layer if the test sample is also substantially transparent (in which case the sensor layer undergoes localized changes from transparent to opaque in the presence of microorganism colonies), it is preferred that the sensor layer not be transparent. Improved results are obtained in detecting microorganisms in test samples that could interfere with detection if the sensor layer is opaque. If the test sample itself interferes with visualizing/ detecting (e.g. with the eye or with an instrument) the presence or growth of microorganisms directly in the immobilization layer, then it is preferable that at least one of the immobilization layer or the sensor layer (preferably the sensor layer) is capable of blocking detection/visualization of the actual test sample and/or actual microorganisms, and instead detect changes in the sensor layer which correspond to presence/growth of microorganisms in the immobilization layer. The immobilization layer can also be opaque, and in one embodiment of carrying out the invention, the sensor layer, the immobilization layer, and the sample are all opaque.

The sensor comprises a solid composition or membrane, with an indicator medium immobilized on or within it. The sensor layer is preferably located flush against the inside surface of the container, or in the sealing means used to seal the container or attached to the sealing means, such that the sensor layer is visible from outside. It is preferably affixed to the container to prevent cells, proteins, other solids or other opaque or colored components from getting between it and the container surface. In certain embodiments the sensor layer is separated from the specimen and its growth medium by a membrane or other solid layer.

One embodiment of this invention comprises a sealing means, such as a lid or cap, which may be transparent or which may have a transparent section. The sensor can be placed in proximity to the transparent lid or section of lid or is made part of the lid. When the lid is used to seal the container, the changes in indicator are read through the transparent sealing means. The sealing means may also be made of a material, such as a polymer, which contains encapsulated indicator micelles. A transparent section in either the container or the sealing means is not needed, as long as the material is permeable to the changes caused by metabolism of the microorganisms, and the changes in the indicator are visible on the surface of the sealing means.

Microorganisms in specimens of body fluids, such as blood, containing as few as 1 organism per total sample volume, can be detected using this invention. Such specimens may require a number of days of incubation before the population of organisms reaches a critical level and where a change in a parameter involved in microorganism metabolism can be measured.

The sensor is useful in that: 1) changes in the sensor layer due to microbial metabolism (e.g., increases or decreases in a gas component due to metabolism) are detected from the solid or semi-solid immobilizing layer rather than in the atmosphere over the specimen, 2) because the sensor is affixed to the interior surface of the plate or the closure or sealing means or attached through the outside of the closure or sealing means, measurements can be made from outside the transparent wall of the plate or the sealing means without having to violate the integrity of the plate, 3) the external measurements can be made by visual inspection or with an instrument that measures by reflectance, fluorescence, etc., or by image capture, 4) opaque/colored or fluorescent components in the specimen do not interfere with the ability to detect changes or the measurement of those changes, and 5) a high concentration of indicator molecules can be maintained within a small volume in the sensor (e.g., within the polymer emulsion or on the membrane), such that a change can be easily observed or detected.

The nutritional components that make up a complex microbial medium influence the metabolic pathways used by microorganisms. Organic acids, bases and various gases are produced in proportions dependent on the nutrients available. These products also vary from species to species of microorganism. The presence of these products in the immobilizing layer can change its pH. The sensor layer used in the invention could contain pH sensitive indicators that give a measurable change in response to a pH change. Or, the presence of gases that affect the pH of the indicator, such as $Co_2$, could be measured. Microbial growth can also be detected by measurement of changes in $O_2$ and/or fluorescence. The sensor layer can be designed to respond to decreases in $O_2$ concentration due to metabolism of microorganisms. And an indicator could be selected that undergoes a change in fluorescence rather than a change in color or other parameter. Carbon dioxide is a common metabolite produced by most organisms and, therefore, is the preferred metabolite for detection of microbial growth. Whatever mechanism is utilized, in a preferred embodiment, the sensor layer will undergo a detectable change in response to the presence/growth of most microorganisms.

The indicator can be attached either covalently or non-covalently to a support medium. Alternately, the indicator can be encapsulated within a polymer matrix such as being emulsified within a polymer matrix prior to curing.

The sensor layer is preferably affixed inside a suitable transparent vessel or a transparent sealing means, with an appropriate adhesive, if necessary. They may also comprise an integral part of the sealing means or be affixed to the sealing means or within the vessel as an indicator emulsified within a polymer matrix cured in situ. They can also be placed outside the container, as long as a method is provided that allows the metabolic changes due to the microorganisms, to affect the sensor.

A variety of different fluorescent and visible pH indicators can be used as the active molecular species in pH, $H_2$, $H_2S$, $NH_3$, $O_2$ or $CO_2$ sensors. Generally, the only limitations on the selection of indicators are the requirements that they have acceptable dynamic ranges and wavelength changes that are detectable by infrared, fluorescence, reflectance and/or imaging technologies.

Sensors for detecting pH changes in the culture medium according to the invention preferably exhibit a change in fluorescence intensity or visible color over a pH range of about 5.0 to about 8.0.

Indicators for a $CO_2$ sensor should exhibit a change in infrared intensity, fluorescence intensity or visible color preferably between about pH 13 and about 5, and most preferably between about pH 13 to about 9, in order to detect changes in $CO_2$ concentration.

Only certain pH indicator molecules can be bound covalently or non-covalently to a support medium and retain their pH indicating properties. Indicators belonging to the xanthene, phenolphthalein and phenolsulfonphthalein groups are useful. Examples of these include fluorescein, coumarin, phenolphthalein, thymolphthalein, bromothymol blue, thymol blue, xylenol blue, ortho cresolphthalein and α-naphthol benzein.

The support medium can be a substance such as cellulose or certain silicones, to which a pH indicator can be covalently attached using organic reactions. Non-covalent attachment of pH indicators can be achieved using ionic support materials, such as nylon membranes that have a positive or negative zeta potential. Other ionic support materials that can be used are positive or negatively charged ionic resins, such as diethylamino ethyl (DEAE) resin or DEAE cellulose. Pretreatment of the support material with a protein may be required if the indicator membrane is to be in direct contact with microbial growth medium.

The pH indicator sensors directly detect pH changes due to the pH environment of the microbial growth medium. However, these sensors can be made to selectively react to gases (e.g., carbon dioxide, ammonia, hydrogen, hydrogen sulfide, or oxygen) due to microorganism metabolism. A selectively semi-permeable composition or membrane could be provided on the sensor layer, such as silicone, latex, teflon, or various plastics characterized by the capacity to selectively permit the diffusion of a gas while preventing the passage of ions. For sensors comprising indicator encapsulated within a polymer matrix, the polymer forming the matrix can act as the semi-permeable barrier that permits the passage of gases but not ions.

In one embodiment, the $CO_2$ sensor is comprised of a plurality of components. The first component is a visual or fluorescent pH indicator, which is reactive at the pH range between 6 and 10. Examples of indicators meeting these criteria are bromothymol blue, thymol blue, xylenol blue, phenolphthalein, ortho cresolphthalein, coumarin, and fluorescein. A second component, if necessary, is an acid, base or buffer, which maintains an optimal pH environment for detection of $CO_2$ by the selected pH indicator. A third component can be glycerol or an equivalent emulsifier, which can produce droplets of indicator solution emulsified within the uncured polymer. A fourth component can be a pigment, such as titanium oxide, zinc oxide, magnesium oxide, ferrous oxide, etc. A fifth component can be an uncured polymer such as silicone, which maintains a proper environment for the indicator. Any polymer can be used that does not affect too greatly the chemical activity of the indicator, either from its own chemical or physical properties or its requirements for curing, as long as it is permeable to gases but not ions, and does not have these properties altered when subjected to sterilization. Other silicone polymers that are also satisfactory are those that are cured by high temperature, by catalytic activity, or by ultraviolet vulcanization. An emulsion is prepared from the various components and the polymer is cured to form a semipermeable matrix around the droplets of pH indicator, which permits selective diffusion of $CO_2$ and other gases from the immobilization layer, resulting in localized measurable changes ill the sensor layer. The sensor layer can be prepared separately, such as in a mold, cured, and then attached to the plate with an appropriate adhesive, such as a silicone adhesive. Alternatively, and preferably, the sensor is formed on the bottom of the container and cured in situ. After curing, the container with the sensor can be sterilized, such as by autoclaving or gamma radiation. Conveniently, the immobilizing and additional optional layers can be introduced into the sensor plate device before sterilization and thus also sterilized by that process.

In a further example, the sensor layer comprises an indicator solution emulsified in a pigmented silicone matrix. The indicator solution is comprised of thymol blue indicator (0.65 g) dissolved into a solution of 0.8 M potassium hydroxide (10.0 ml) and isopropyl alcohol (10.0 ml). The indicator solution (5.0 g) is then mixed with the pigmented silicone components. The pigmented silicone matrix is comprised of Sylgard 184 silicone (components A (50.0 g) and B (5.0 g)) and white pigment (part #61-18000, Ferro Corp., New Jersey) (1.0 g). The sensor material is then poured and spread onto a plate in a thin layer (approximately 0.2 to 0.5 mm).

In another example, the sensor layer comprises an indicator solution mixed with a pigmented silicone matrix. The indicator solution is comprised of ortho-cresolphthalein indicator (2.0 g) dissolved into a solution of isopropyl alcohol (5.0 ml) and 0.9 M potassium hydroxide (5.0 ml). The indicator solution (2.5 g) is then mixed with the pigmented silicone components. The pigmented silicone matrix is comprised of Sylgard 184 silicone (components A (25.0 g) and B (2.5 g)) and white pigment (part #61-18000, Ferro Corp., New Jersey) (0.5 g). The sensor material is then poured and spread onto a plate in a thin layer (approximately 0.2 to 0.5 mm). In a variation of this example, the above ortho-cresolphthalein sensor layer is covered with an overcoat layer comprising the pigmented silicone matrix.

In still another example, the sensor layer is composed of an indicator solution mixed with a pigment solution and a silicone matrix. The indicator solution is comprised of ortho-cresolphthalein indicator (2.0 g) dissolved into a solution of isopropyl alcohol (10.0 ml), and 0.8 M potassium hydroxide (10.0 ml). The pigment solution is comprised of silicone oil (40.0 g), white pigment (part #61-18000, Ferro Corp., New Jersey) (4.0 g). The silicone matrix is comprised of Wacker Elastosil RT 601 silicone (components A (200.0 g) and B (20.0 g)) and toluene (40.0 g). The indicator solution (20.0 g) is then mixed with the pigment solution (40.0 g) and silicone components. The sensor material is then sprayed onto a plate in a thin layer (approximately 0.1 to 0.3 mm thick).

In addition to indicators responsive to changes in oxygen, carbon dioxide and pH, as mentioned above, indicators could also be utilized that detect changes in ammonia, oxidation-reduction potential, hydrogen, hydrogen-sulfide, or any other substance that undergoes a change due to the presence or growth of microorganisms. Also, a plurality of different indicators could be used in the sensor layer (or in a plurality of sensor layers).

The sensor layer is preferably opaque so as to prevent properties of the sample (e.g. natural fluorescence, opacity, etc.) from affecting or masking the response of the sensor. The sensor layer preferably changes from one opaque state to another opaque state in the presence of microorganisms, with the change being a detectable change by image capture and processing. As one example, the sensor layer could be an emulsified mixture of ortho cresolphthalein indicator in a white pigmented silicone matrix, with an overlay of white pigmented silicone. Or, the sensor layer could be a pigmented silicone matrix emulsified with one or more indicators such as thymol blue indicator, a xylenol blue indicator, or a "universal" indicator. The matrix in the sensor layer could be a suitable latex, polyurethane, nylon membrane (e.g. charged nylon membrane) or cellulose powder. The sensor layer matrix could also be a silicone matrix, such as Sylgard 184, Wacker 601, or Wacker 934. Or, the sensor layer could be made up of two layers, such as an indicator layer and an opaque layer.

The other main layer in the sensor plate device is the immobilizing layer 10. The purpose of the immobilizing layer is to immobilize organisms in the sample either within a matrix or on the surface of a matrix. The sample itself can be a liquid, semi-solid or semi-liquid (e.g. paste or gel) sample. A liquid sample can be mixed with a dry powdered gelling agent to form an organism-immobilizing gel matrix when mixed. The liquid sample is preferably added to a dry powdered gelling agent already provided as a layer in the sensor plate device. However, a liquid sample could also be mixed with a dry powdered gelling agent, and then both immediately added to the sensor plate device before gelling has occurred. Also, a liquid sample could be applied onto an already gelled matrix, or onto a dehydrated or partially dehydrated gel matrix so as to immobilize the microorganisms on the surface of the gel. A gelling agent could also be imbedded in a support matrix to add physical support. Examples include glass or cellulose synthetic polymer fibers either mixed throughout or in the form of woven or nonwoven fabrics. Also, in order to immobilize a sample, the immobilization layer need not be a gelling agent, but rather-could comprise a non-gel absorbent material, such as sponge materials, celluloses, glass fibers, filter paper, etc.

More than one gelling agent could be utilized in the sensor plate device, either mixed together or as separate layers. For example, a mixture of guar gum and xanthan gum, combined by weight at an approximate ratio of 2:1, could be used. Other gelling agents could be used singly or in combination, including natural and synthetic hydrogel powders. One or more gelling agents could be combined together selected from gums, agars, agaroses, carageenans, bentonite, alginates, collagens, gelatins, fused silicates, water soluble starches, polyacrylates, celluloses, cellulose derivatives, polyethylene glycols, polyethylene oxides, polyvinyl alcohols, dextrans, polyacrylamides, polysaccharides or any other gelling or viscosity enhancing agents.

Dehydrated and/or partially dehydrated gel matrices for surface colony isolation/immobilization could be used, including one or more synthetic or natural hydrophilic polymers. If more than one gelling agent is used, such could be mixed together or provided in a plurality of layers. In one example, an upper layer could be provided to trap microorganisms on the surface, and a lower layer could be provided as a wicking agent to draw the liquid sample through the upper layer (e.g. a thin agar layer over a modified cellulose absorbent, or a porous hydrophilic membrane over an absorbent pad, polymer or hydrogel).

The immobilization layer must not adversely affect the sensor layer. If the sensor layer undergoes a detectable change due to a pH change, then a very acidic gel layer could adversely affect the sensor layer (also some manufacturing processes are acidic and could leave an acid residue that could adversely affect the sensor layer). Furthermore, if the immobilization layer is a powdered gel layer, it should be certain that this layer does not turn acidic when mixed with a blood sample, as this could also cause the sensor layer to change even in the absence of microorganisms.

As can further be seen in FIG. 2, an optional conditioning layer 16 can be provided on (or within or below) the immobilizing layer. Though illustrated separate from the immobilization layer in FIG. 2, the conditioning materials from the conditioning layer are preferably incorporated into the immobilization layer itself. Conditioning components, whether provided within the immobilization layer or in a separate layer, can include one or more of media for microorganism growth, lytic agents, lytic enzymes, antibiotic neutralizers, surfactants or other materials helpful for improving microorganism detection capabilities. Conditioning components can also be provided both within the immobilization layer and in a separate layer in the same sensor plate device.

Lytic agents for conditioning can be added for lysing blood cells in the test sample, for allowing for a smoother gel, and/or for better rehydration of the gel. Examples of possible lytic agents include saponin, digitonin, Tweens™, polysorbitan monolaurate, and other surfactants. Lytic enzymes, typically though not necessarily proteolytic enzymes, may be added for digesting cellular material in a blood sample, for making a smoother gel, and/or for better rehydration of the gel. The lytic enzymes for conditioning can include one or more proteases, for example an enzyme mixture derived from *Aspergillus oryzae*, or the like.

Antibiotic neutralizers may be added for conditioning, in particular for faster and/or better recovery of microorganisms in the test sample. One or more of such neutralizers could be selected from resins, gums, and carbon-based materials (e.g. activated charcoal or Ecosorb®), or one of a variety of enzymes to specifically degrade various antibiotics (e.g. beta lactamase).

Media can also be added for conditioning (whether directly to the immobilization layer or separately). Media is added to provide nutrients for the growth of microorganisms. Though many types of media for different types of microorganisms could be used, if the microorganism is an aerobic organism, the media could include, as one example (an exemplary amount of each being listed in parentheses in g/l): tryptone (17), soytone (3), proteose peptone (5), malt extract (2.5), dextrose (2.5) and MOPS (23). If the microorganism is an anaerobic organism, the media could further include the media listed above for aerobic organisms, as well as Hemin (0.005), L-cystine (0.2), Na-m-bisulfide (0.2) and Menadione (0.0005).

For Coliforms, the media could include, as an example, Lactose (5), bile salts #3 (0.8), $K_2HPO_4$ (7), $KH_2PO_4$ (3), $(NH_4)_2SO_4$ (0.5), $MgSO_4$ (0.1), Na-m-bisulfide (0.4) and SDS (0.1). For yeast, mold and other acid tolerant microorganisms, the media could include, as one example, dextrose (10), yeast extract (10), ($NH_4$) citrate (2) and tartaric acid to a pH of 5.5.

As can be further seen in FIG. 2, a wall of the container can be provided with apertures 20, below which is a hydrophobic gas-permeable film 22, and above which is a gas-impermeable (removable) film 24. Or, the container could be provided with an opening in a wall thereof with the gas-impermeable film and the hydrophobic gas-permeable film adhered together covering the opening. If the organism is anaerobic, the gas-impermeable film would be left in place. However, if the organism is aerobic, the gas-impermeable film would be removed at the time of the addition of a test sample to the sensor plate device. Of course, the hydrophobic gas-permeable film need not be provided at all, though it is beneficial for preventing contaminants from entering the container, and for preventing potentially infectious test material from leaking out of the device.

Figure 3:
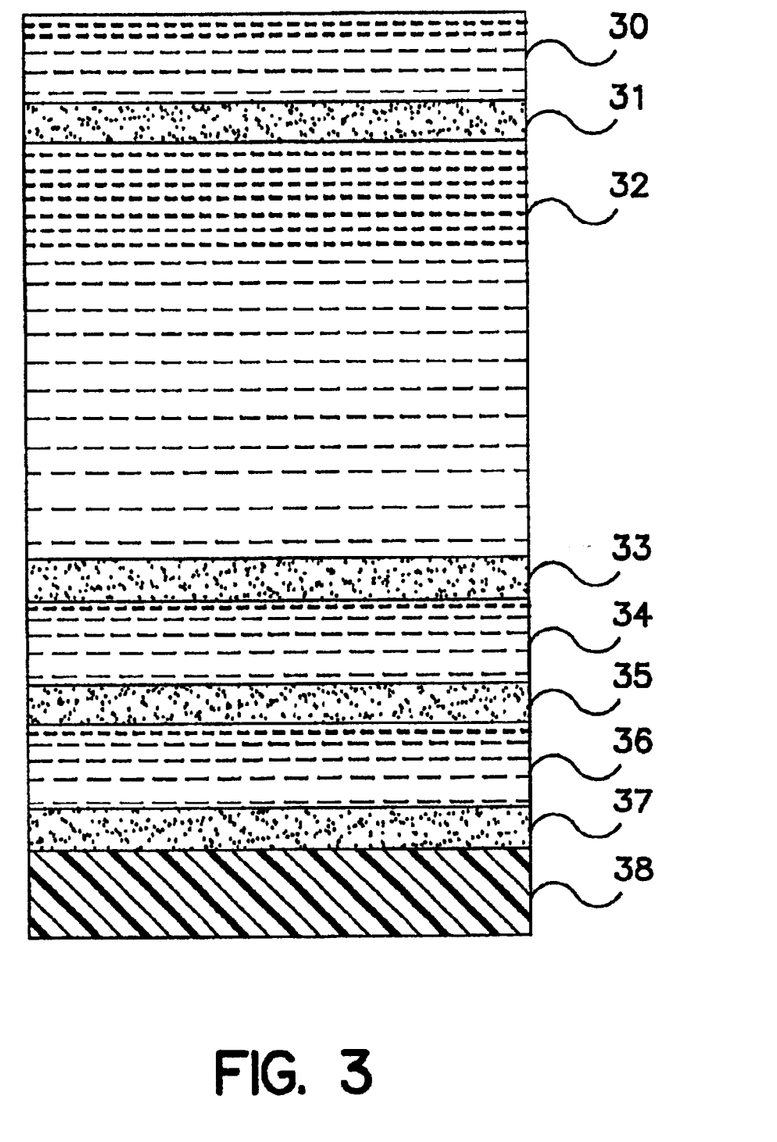
FIG. 3 is a cross section of an alternative embodiment of the sensor plate device.

Area A in FIG. 2 is illustrated in further detail in FIGS. 3 and 4. As can be seen in FIG. 3, in a further embodiment of the sensor plate device, in place of a single immobilization matrix layer, there can be provided one or more of: an isolation gel layer 30 for a semi-rigid surface to allow surface capture and recovery after growth, an adhesive layer 31, an absorptive gel layer 32 and an additional adhesive layer 33. The absorptive gel layer 32 can include one or more of conditioning components (in gels), media for microorganism growth, lytic enzymes, and antibiotic neutralizers. As can be further seen in FIG. 3, in place of a single sensor layer, there can be provided one or more of: an overcoat layer 34, an adhesive layer 35, an indicator layer 36, and an additional adhesive layer 37 in contact with plate bottom 38.

Figure 4:
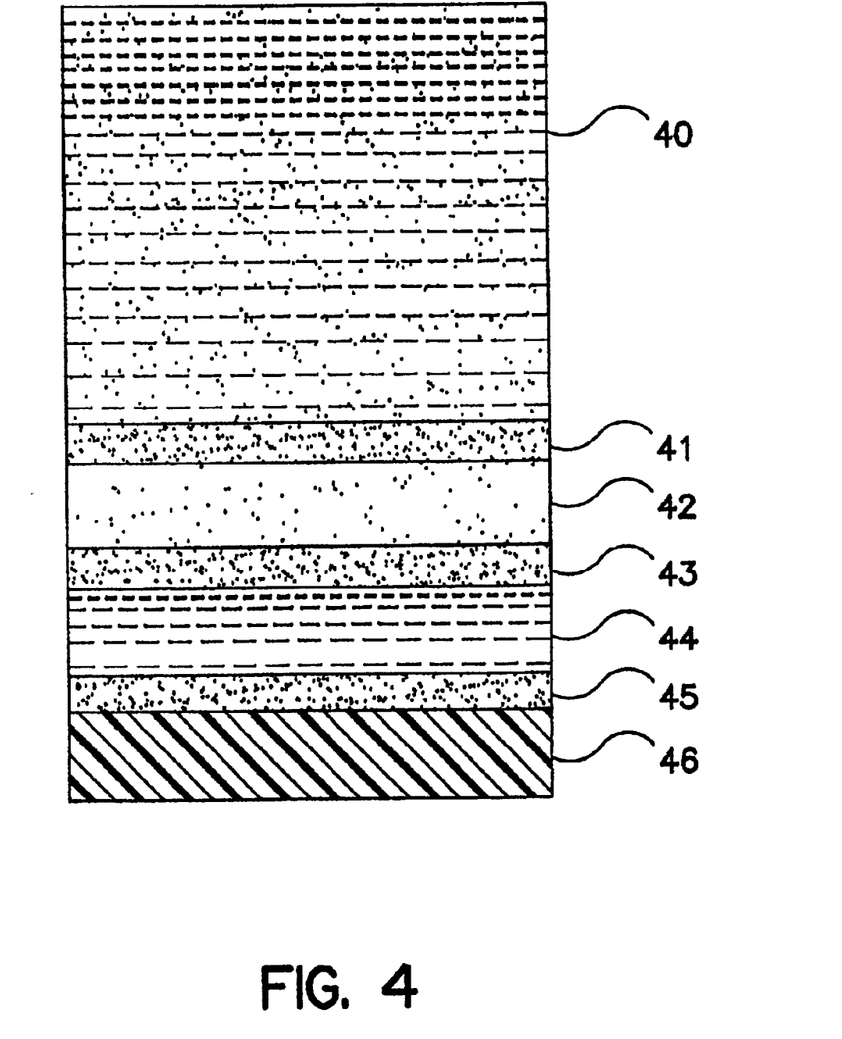
FIG. 4 is a cross section of a further alternative embodiment of the sensor plate device.

In an additional embodiment of the invention as illustrated in FIG. 4, provided is a matrix layer 40 which comprises: a gelling powder, and dry conditioning components such as media, lytic enzymes and antibiotic neutralizers. As in FIG. 3, in place of a single sensor layer, there can be provided one or more of: an adhesive layer 41, an overcoat layer 42, an adhesive layer 43, an indicator layer 44, and an adhesive layer 45 in contact with plate bottom 46.

The size of the sensor plate device can be varied depending upon the desired sample size. In one example, a sensor plate device has an immobilization layer of the dimensions of 74 mm×117 mm. If the immobilization layer comprises a wet-type gel, then the sample size could be made very small (e.g. 1 ml or less), or, such as with a blood sample, the sample size could be up to 15 ml. On the other hand, if the immobilization layer comprises a dry powdered gel, then the sample size could be even greater, depending upon the amount of the powdered gel (e.g. the sample could be 30 ml or more).

In use, a fluid sample is introduced into the sensor plate device. The sample is "conditioned" (if desired) as it spreads across the bottom surface of the sensor plate. The sample is absorbed into, or forms a gel with, an immobilization matrix layer. The sensor plate is then incubated, promoting the growth of microorganism colonies. A sensor layer located toward a bottom surface of the sensor plate device, undergoes a detectable change so as to indicate the presence of microorganism colonies. Finally, the sensor plate device is inspected manually or automatically to determine the presence and location of microorganism colonies.

If the sensor plate device is inspected automatically, an instrument is provided which performs three main functions: plate incubation, image acquisition/capture, and image processing. The instrument provides a controlled environment for incubating plates, which can include a heater if incubation is to take place at an elevated temperature from ambient (though an elevated temperature is not necessary in all situations). A fluid sample is added to the sensor plate device, after which the sensor plate is placed in the instrument where it is subsequently sensed/observed by an image acquisition/capture device (e.g. a camera or scanner) during the incubation period. Images of the bottom of the sensor plate device can be captured at regular predetermined intervals and subsequently analyzed using one or more image processing techniques and algorithms to determine whether a microorganism colony is present on the sensor plate.

Figure 5:
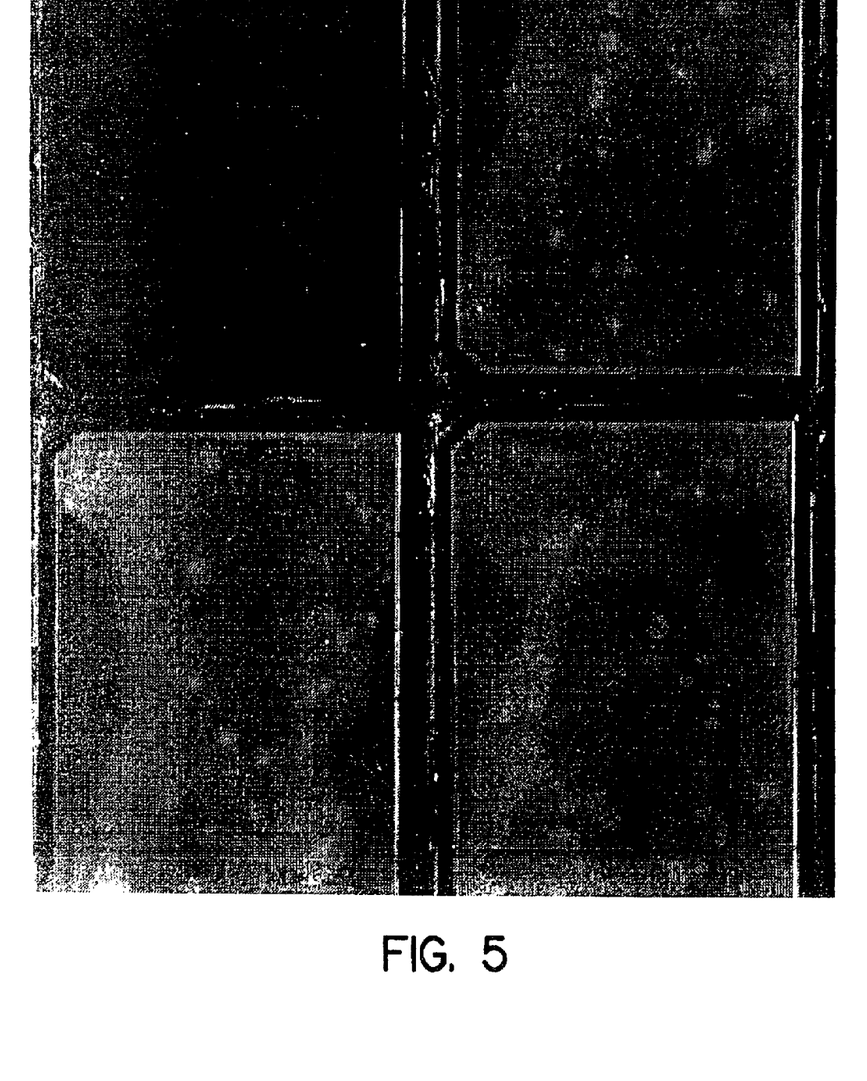
FIG. 5 shows the bottom of three sensor plates positive for E. coli.

Feasibility studies of a number of different types of sensor plate devices have shown good detection results: *E. coli* detected in approximately 9 hours, *E. facaelis* detected in about 10 hours, and *S. aureus* detected in about 11 hours. FIG. 5 shows the underside of four sensor plates where the sensor layer has undergone a detectable change in those areas of the sensor layer proximate to microorganism colonies in an adjacent immobilization matrix layer. Detected colonies in the studies subsequently yielded microbial dilutions which were immediately usable for further testing.

We claim:

1. A sensor device comprising:

a container having at least one wall which is configured such that it is optically visible therethrough to define an optical detection portion;

a sensor layer having first and second primary surfaces disposed in said container adjacent said container wall, wherein said sensor layer comprises a support material and an indicator material, said indicator material selected for its ability to undergo a change in a detectable property when positioned proximate microbial growth that is external of the bounds of the sensor layer, and wherein said sensor layer is configured, during operation, so as to provide a localized change in reflected ultraviolet, visible, and/or infrared light due to the presence of microorganisms in said container corresponding to an immobilized sample residing outside the sensor layer so that the microbial growth is beyond the bounds of the sensor layer which is detectable through said container wall optical detection portion.

2. A device according to claim 1, wherein said sensor layer is opaque.

3. A device according to claim 1, wherein said container wall is one of transparent and translucent.

4. A device according to claim 1, wherein said sensor layer undergoes a detectable change in response to changes in the container of at least one of oxygen, hydrogen, hydrogen sulfide, carbon dioxide, ammonia, organic acid, nitrogen dioxide, and pH.

5. A device according to claim 4, wherein, during use, said sensor layer indicator undergoes a change which is detectable by at least one of imaging, fluorescence and reflectance detection.

6. A device according to claim 5, wherein said sensor layer undergoes a change such that it is able to exhibit a change in fluorescence intensity or visible color over a pH range of about 5.0 to 11.0.

7. A device according to claim 1, wherein said sensor layer is an opaque layer with a color which changes in intensity in the presence of microorganisms.

8. A sensor device comprising:

a container configured to receive a quantity of a liquid sample to be tested for the presence, enumeration and/or concentration of microorganisms;

a sensor layer having a color, translucence, and/or opacity associated therewith disposed in said container such that, in operation, said sensor layer is exposed to microbial growth in said sample occurring outside the bounds of the sensor layer, and wherein localized regions of said sensor layer change in color and/or intensity corresponding to a detection of actual microorganism colony growth from the sample, and wherein, during use, the container is adapted to transform the liquid sample into an immobilized state above the sensor layer so that the microorganism grow above the sensor layer.

9. A device according to claim 8, wherein said sensor layer is opaque.

10. A device according to claim 8, wherein said container wall is one of transparent and translucent.

11. A device according to claim 8, wherein said sensor layer undergoes a detectable change in response to changes in the container of at least one of oxygen, hydrogen, hydrogen sulfide, carbon dioxide, ammonia, organic acid, nitrogen dioxide, and pH.

12. A device according to claim 8, wherein during use, said sensor layer indicator undergoes a change which is detectable by at least one of imaging, fluorescence and reflectance detection.

13. A device according to claim 8, wherein said sensor layer undergoes a change such that it is able to exhibit a change in fluorescence intensity or visible color over a pH range of about 5.0 to 11.0.

14. A device according to claim 8, wherein said sensor layer is an opaque layer with a color which changes in intensity in the presence of microorganisms.

15. A sensor device comprising:
a solid substrate having opposing first and second primary surfaces;
a sensor layer disposed onto said first primary surface of said substrate, wherein said sensor layer comprises an indicator encapsulated within a polymer matrix, wherein, during use, said polymer forming the matrix acts as a semi-permeable barrier, and wherein, during use, said sensor layer indicator is configured to indicate detectable changes in regions in said sensor layer which correspond to microorganism colony growth outside the sensor layer; and
a non-flowable immobilization layer disposed proximate said sensor layer on the side opposing said solid substrate, wherein the immobilization layer is configured to immobilize a sample outside the bounds of the sensor layer, and wherein the detectable changes in the sensor layer correspond to growth in and/or on the immobilization layer outside the bounds or the sensor layer.

16. A sensor device according to claim 15, wherein said sensor layer comprises a support material and an indicator material, said indicator material selected for its ability to undergo a change in a detectable property when positioned proximate microbial growth, and wherein said sensor layer is configured, during operation, so as to provide a localized change in the ultraviolet, visible, and/or infrared spectrum due to the presence of microorganisms.

17. A device according to claim 15, wherein said sensor layer is opaque.

18. A device according to claim 15, wherein said container wall is one of transparent and translucent.

19. A device according to claim according to claim 15, wherein said sensor layer undergoes a detectable change in response to changes in the container of at least one of oxygen, hydrogen, hydrogen sulfide, carbon dioxide, ammonia, organic acid, nitrogen dioxide, and pH.

20. A device according to claim 16, wherein, during use, said sensor layer indicator undergoes a change which is detectable by at least one of imaging, fluorescence and reflectance detection.

21. A device according to claim 15, wherein said sensor undergoes a change such that it is able to exhibit a change in fluorescence intensity or visible color over a pH range of about 5.0 to 11.0.

22. A device according to claim 15, wherein said sensor layer is an opaque layer with a color which changes in intensity in the presence of microorganisms.

* * * * *